(12) United States Patent
Junginger et al.

(10) Patent No.: US 8,169,210 B2
(45) Date of Patent: May 1, 2012

(54) CONTACTLESS SYSTEM AND METHOD FOR ELECTROSTATIC SENSING WITH A HIGH SPATIAL RESOLUTION

(75) Inventors: Johann Junginger, Toronto (CA); Markus R. Silvestri, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 497 days.

(21) Appl. No.: 12/419,907

(22) Filed: Apr. 7, 2009

(65) Prior Publication Data

US 2010/0253358 A1    Oct. 7, 2010

(51) Int. Cl.
*G01R 31/02* (2006.01)
*G01N 27/60* (2006.01)
(52) U.S. Cl. ................................. 324/72; 324/456
(58) Field of Classification Search .............. 324/72, 324/456
See application file for complete search history.

(56) References Cited

U.S. PATENT DOCUMENTS

| | | | |
|---|---|---|---|
| 4,265,990 A | | 5/1981 | Stolka et al. |
| 4,330,749 A | * | 5/1982 | Eda et al. .................. 324/457 |
| 5,241,276 A | * | 8/1993 | Tanaka et al. ............. 324/452 |
| 5,675,993 A | * | 10/1997 | Ono et al. ................... 66/204 |
| 6,008,653 A | | 12/1999 | Popovic et al. |
| 6,119,536 A | | 9/2000 | Popovic et al. |
| 6,185,991 B1 | * | 2/2001 | Hong et al. ................. 73/105 |
| 7,271,593 B2 | | 9/2007 | Junginger et al. |
| 7,675,293 B2 | * | 3/2010 | Christophersen et al. .... 324/613 |

* cited by examiner

*Primary Examiner* — Jeff Natalini
(74) *Attorney, Agent, or Firm* — Pillsbury Winthrop Shaw Pittman LLP (57) ABSTRACT

In the illustrated embodiment of the invention a scanning system is provided for scanning a chargeable surface for latent image detection. The chargeable surface is charged to a first potential, and a scanner probe is charged to a second potential within a predetermined potential difference from the first potential. The scanner probe is oscillated at a selected frequency and reads or measures the oscillation current that is induced from the oscillation and detects any latent images or other electrostatic distributions on the chargeable surface. A processor processes the probe measurements for determining the potential of a latent image on the chargeable surface based on the scanner probe readings.

20 Claims, 4 Drawing Sheets

CONTACTLESS SYSTEM AND METHOD FOR ELECTROSTATIC SENSING WITH A HIGH SPATIAL RESOLUTION

BACKGROUND

The invention relates to the field of a scanning system for detecting defects in a chargeable surface. In particular, this disclosure relates to a contactless system and method for sensing electrostatic surface potentials with very high spatial resolution.

In the art of xerography, a xerographic plate or photoreceptor having a photoconductive insulating layer is provided. An image is acquired by first uniformly depositing an electrostatic charge on the imaging surface of the xerographic plate and then exposing the plate to a pattern of activating electromagnetic radiation, such as light, which selectively dissipates the charge in the illuminated areas of the plate while leaving behind an electrostatic latent image in the non-illuminated areas. This electrostatic latent image may then be developed to form a visible image by depositing finely divided electroscopic marking particles on the imaging surface. It is important in research and development, engineering and quality control to be able to detect the latent image with a high spatial resolution prior to development with toner. Additionally, high spatial resolution also increases the accuracy of results obtained when studying lateral charge migration (LCM), a subset of the stability, accuracy and uniformity of the charge distributions that make up the latent image.

A photoreceptor layer for use in latent image detection in xerography or in latent image studies may be a homogeneous layer of a single material such as vitreous selenium, or it may be a composite layer containing a photoconductor and another material. One type of composite photoconductive layer commonly used in photoreceptors is described in U.S. Pat. No. 4,265,990, the entire disclosure thereof being incorporated herein by reference. The patent describes a photosensitive member having at least two electrically operative layers. One layer comprises a photoconductive layer which is capable of photo-generating holes and injecting the photogenerated holes into a contiguous charge transport layer. Generally, where the two electrically operative layers are positioned on an electrically conductive layer with the photoconductive layer sandwiched between a contiguous charge transport layer and the conductive layer, the outer surface of the charge transport layer is normally charged with a uniform electrostatic charge, and the conductive layer is utilized as an electrode. In flexible electrophotographic imaging members, the electrode is normally a thin conductive coating supported on a thermoplastic resin web.

The conductive layer may also function as an electrode when the charge transport layer is sandwiched between the conductive layer and a photoconductive layer which is capable of photogenerating electrons and injecting the photogenerated electrons into the charge transport layer. The charge transport layer in this embodiment must be capable of supporting the injection of photogenerated electrons from the photoconductive layer and transporting the electrons through the charge transport layer. The photoreceptors are usually multilayered and comprise a substrate, an optional conductive layer (if the substrate is not itself conductive), an optional hole blocking layer, an optional adhesive layer, a charge generating layer, and a charge transport layer and, in some belt embodiments, an anti-curl backing layer.

One of the first techniques for electrostatic sensing was the stylus scanner. This technology had high resolution, as limited by the stylus diameter, but was not suitable for scanning larger areas due to its overall low speed.

Next came the charge deficient spot (CDS) scanner which was developed to address the low speed limitation of the previous stylus scanners. However with the CDS scanner, it was noted that variations in the air gap distance introduced some measurement errors.

The implementation of aerodynamic floating, or the floating probe scanner (FPS) enabled the ability to better control the air gap distance, improving the overall accuracy of the measurement.

From here, two different development branches for this technology began to take shape. The first branch consisted of FPS's with look-up-table corrections for small non-uniformities in gap distance which could be used to study charge deficient spots (CDS's), which are point-like electrical defects in the photoreceptor surface or bulk. This measurement requires knowledge of the air gap for each measurement point and is determined through some signal-processing operations and a pre-determined calibration curve. These innovations were disclosed in U.S. Pat. No. 7,271,593 which is incorporated herein by reference in its entirety. The second branch has led to high resolution electrostatic (floating probe) scanners (Hi-RES) and the current invention described in detail below.

Another technique for sensing electrostatic surface potentials has been the use of current generation non-contact electrostatic voltmeters (ESV). Such devices such as those made by Trek, Inc. such as the Trek 344 with a Trek 6000B-8 probe, or the Trek 368A with a Trek 3800E-2 probe, are well known to those in the xerography community and are relatively inexpensive, can scan large amounts of area, and readily suitable for general xerography. However, ESV devices have spatial resolution that is only on the order of millimeters, which is unsuitable for LCM studies.

Another technique for sensing electrostatic surface potentials has been the use of atomic force microscopy (AFM). AFM devices provide very high spatial resolutions of up to 1 µm, however they are very expensive to install and use and can only scan small amounts of area at a time which makes them highly undesirable for applications such as latent image detection in xerography or latent image studies.

However in the context of product development or quality control, machine sensing of electrostatic surface potentials is a laborious and time consuming process involving hand feeding of sheets by test personnel along with constant monitoring of the final quality of every sheet. The prior art technology is unsuitable for product development or quality control applications because the charge amplifier sub-system is only sensitive to transient events, such as when a point-like defect is detected. The corrected floating probe scanners cannot resolve the electrostatic potential when uniform over large areas due to the AC-coupled nature of the charge amplifier. Moreover, accuracy of the test results depends a great deal upon interpretations and behavior of the personnel that are feeding and evaluating the sheets.

Further, since machine characteristics vary from machine to machine for any given model or type, reliability of the final test results for any given machine model must factor in peculiar quirks of that specific machine versus the characteristics of other machines of the same model or type. Because of machine complexity and variations from machine to machine, the data from a test in a single machine is not sufficiently credible to justify the scrapping of an entire production batch of photoreceptor material.

Thus, tests are normally conducted in three or more machines. Since a given photoreceptor may be used in different kinds of machines such as copiers, duplicator and printers under markedly different operating conditions, the sensing of electrostatic surface potentials based on the machine tests of a representative test photoreceptor sample is specific to the actual machine in which photoreceptors from the tested batch will eventually be utilized. Thus, photoreceptor tests on one machine do not necessarily predict whether the same electrostatic surface potential will occur if the same type of photoreceptor were used in a different type of machine.

Thus, for a machine latent image test, the test would have to be conducted on each different type of machine. This becomes extremely expensive and time consuming. Moreover, because of the length of time required for machine testing, the inventory of stockpiled photoreceptors waiting approval based on life testing of machines can reach unacceptably high levels. For example, a batch may consist of many rolls, with each roll yielding thousands of belts.

One test method utilizes a stylus scanner such as that described by Z. D. Popovic et al., "Characterization of Microscopic Electrical Defects in Xerographic Photoreceptors", Journal of Imaging Technology, vol. 17, No. 2, April/May, 1991, pp. 71-75. The stylus scanner applies a bias voltage to a shielded probe, which is immersed in silicone oil and is in contact with the photoreceptor surface. The silicone oil prevents electrical arcing and breakdown. Current flowing through the probe contains information about defects, and scanning speeds up to 6×6 mm2 in about 15 minutes were achieved. Although the stylus scanner is a highly reproducible tool which enabled some important discoveries, it has the basic shortcoming of low speed.

Many attempts have also been made in the past to reduce the time of scan by designing contactless probes. For example, a probe has been described in the literature and used for readout of xeroradiographic (X-ray) amorphous selenium plates, (see, e.g., W. Hillen, St. Rupp, U. Schieble, T. Zaengel, Proc. SPIE, Vol. 1090, Medical Imaging III, Image Fonnation, 296 (1989); W. Hillen, U. Schieble, T. Zaengel, Proc. SPIE, Vol. 914, Medical Imaging II, 253 (1988); and U. Schieble, T. Zaemge, Proc. SPIE, Vol. 626, Medicine XIV/PACS IV, 176 (1986)). These probes rely on reducing the distance of a probe to a photoreceptor surface in order to increase resolution of the measurements. The typical distance of the probe to the photoreceptor surface is 50-150 micrometers. In order to avoid air breakdown, the ground plane of a xeroradiographic plate is biased appropriately to provide approximately zero voltage difference between the probe and photoreceptor surface.

In U.S. Pat. Nos. 6,008,653 and 6,119,536, the contents of both of which are incorporated herein by reference in their entirety, a contactless system and method for scanning a photoreceptor surface is described. In U.S. Pat. No. 6,008,653, entitled CONTACTLESS SYSTEM FOR DETECTING MICRODEFECTS ON ELECTROSTATOGRAPHIC MEMBERS, a contactless process is disclosed for detecting surface potential charge patterns in an electrophotographic imaging member, including applying a constant voltage charge to an imaging surface of a photoreceptor, and biasing a capacitive scanner probe having an outer shield electrode to within about ±300 volts of the average surface potential of the imaging surface. The probe is maintained adjacent to and spaced from the imaging surface to form a parallel plate capacitor with a gas between the probe and the imaging surface. Relative movement is established between the probe and the imaging surface, maintaining a substantially constant distance between the probe and the imaging surface. The probe is synchronously biased and variations in surface potential are measured with the probe. The surface potential variations are compensated for variations in distance between the probe and the imaging surface. The process described in U.S. Pat. No. 6,008,653 is implemented using a system for maintaining a substantially constant distance between the probe and the imaging surface. This system is described in U.S. Pat. No. 6,119,536, entitled CONSTANT DISTANCE SCANNER PROBE SYSTEM. While ideally the distance between the probe and the imaging surface is maintained constant while scanning the imaging surface, in reality small variations do occur. An algorithm is provided for compensating for variation in the distance between the probe and the imaging surface. The algorithm is based on compensation for a flat plate capacitor in which a known time-varying reference charge (or voltage) is applied to the drum or conductive substrate of the material-under-test and is uniformly spatially distributed below the probe surface. However, when studying and analyzing the latent image, the charge distribution on a surface can be non-uniform.

Another technique related to sensing electrostatic surface potentials can be found in U.S. Pat. No. 7,271,593, entitled CONTACTLESS SYSTEM AND METHOD FOR DETECTING DEFECTIVE POINTS ON A CHARGEABLE SURFACE, the entire disclosure thereof being incorporated herein by reference. The patent describes a device and method for detecting charge deficient spots (CDS's) in a latent image on a photoreceptor for use in xerography. The disclosed device makes use of a chargeable photoreceptor surface held at a first voltage, the surface of a probe held at a second voltage, determining the potential of a CDS on the chargeable surface based on received readings from the probe, and then applying a reference charge to the chargeable surface and thus correcting the CDS. Furthermore, the current device includes higher order mathematical corrections to account for the point-like nature of the CDS's.

While the methods discussed here are highly effective for detecting transient events such as a CDS, which appear as small, spatially localized discharged spots or defects on the uniformly charged photoreceptor surface, the apparatus or instrument described detects transient changes in the surface voltage, as caused by a CDS. The disclosed devices and methods of the prior art are not capable of sensing absolute surface voltage. The current invention detects the absolute surface voltage through the vibration of the probe, a feature which is strongly desired when detecting a latent image for xerography purposes or when studying latent images.

Thus, there is a need for a system and a method which directly measures charge migration or surface voltage at high resolution, is easy to use, and can be immediately implemented into photoreceptor research.

SUMMARY

The following embodiments provide for a contactless system for sensing electrostatic potential on a chargeable surface for studying xerographic photoreceptors as well as for applications in materials science, surface science, and quality control comprising a first circuit for charging the chargeable surface to receive and hold a first voltage charge, a scanner probe having a probe surface, the probe surface being displaced a distance from the chargeable surface, a second circuit for biasing the scanner probe to a second voltage charge within a predetermined voltage threshold of the first voltage charge, a capacitor is comprised of the chargeable surface, a dielectric material between the scanner probe surface and the chargeable surface, and the scanner probe surface and wherein the scanner probe senses a potential associated with an applied charge on the chargeable surface. It is not necessary to know the absolute air gap distance between the scanner probe surface and the chargeable surface in the current invention, so long as it remains relatively constant (±20 um variation from the setpoint) and is sufficiently close to the sample under test (50 to 150 um). This makes the system simpler to operate as no distance calibration is required.

The present embodiment further provides a device for oscillating the scanner probe at a frequency of the probe to induce an oscillating current in the scanner probe defined as a scanner probe reading, a third circuit for sensing the induced oscillating current in the scanner probe, a processor, and a charge determination module including programmable instructions executable by the processor for determining the potential of a specific location on the chargeable surface based on the scanner probe reading and the induced oscillating current in the scanner probe, including charge migration on the chargeable surface, wherein the determination of the potential of a specific location comprises adjusting the scanner probe bias voltage to null the induced oscillating current in the scanner probe.

In another embodiment, there is provided a method for sensing electrostatic potentials on a chargeable surface comprising charging the chargeable surface to receive and hold a first voltage charge, spacing a surface of a scanner probe a distance from the chargeable surface, biasing the scanner probe to a second voltage charge within a predetermined voltage threshold of the first voltage charge, wherein a capacitor is established by a combination of the chargeable surface, a dielectric substance between the scanner probe and the chargeable surface, and the scanner probe, oscillating the scanner probe at a frequency of the scanner probe in order to induce a current in the scanner probe defined as the scanner probe reading, sensing the induced current in the scanner probe, applying a reference charge to at least one of the scanner probe and the chargeable surface, and determining a potential of a specific location on the chargeable surface based on scanner probe reading by adjusting the scanner probe bias voltage to null the induced current in the scanner probe.

In yet another embodiment, there is provided a contactless scanning system for sensing electrostatic potential on a photoreceptor comprising a first circuit for charging the photoreceptor to receive and hold a first voltage charge, a scanner probe having a probe surface, the probe surface being displaced a distance from the photoreceptor, a second circuit for biasing the scanner probe to a second voltage charge within a predetermined voltage threshold of the first voltage charge, wherein a capacitor is established by a combination of the photoreceptor, a dielectric material between the scanner probe surface and the photoreceptor, and the scanner probe, wherein the scanner probe senses a potential associated with an applied charge on the photoreceptor, a device for oscillating the scanner probe at a frequency of the scanner probe in order to induce an oscillating-current in the scanner probe, a third circuit for sensing the induced oscillating current in the scanner probe, a processor; and a charge determination module including programmable instructions executable by the processor for determining a potential of a specific location on the photoreceptor based on the scanner probe reading and the induced oscillating current in the scanner probe, including charge migration on the photoreceptor, a fourth circuit for adjusting the scanner probe bias voltage to null the vibration induced current in the scanner probe.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The present embodiments can be better visualized by turning now to the following drawings wherein like elements are referenced by like numerals.

The present embodiments can now be better understood by turning to the following detailed description of the present embodiments which are presented as illustrated examples of the embodiments defined in the claims. It is expressly understood that the embodiments as defined by the claims may be broader than the illustrated embodiments described below.

DETAILED DESCRIPTION

In the illustrated embodiment, a scanning system is provided for scanning a chargeable surface for latent image detection and lateral charge migration (LCM) testing. The chargeable surface is charged to a first potential, and a scanner probe is charged to a second potential within a predetermined potential difference from the first potential. Additionally, a reference wave is applied to at least one of the scanner probe and the chargeable surface. The scanner probe is oscillated at a frequency and reads or measures the oscillation current that is induced from the oscillation and detects any latent images on the chargeable surface. A processor processes the probe measurements (also referred to as readings) for determining the potential of a latent image on the chargeable surface based on the scanner probe readings including adjusting the determination of the potential of the latent image based on the distance from the probe surface to the chargeable surface to account for the non-uniform charge distribution that may be present on the chargeable surface.

The illustrated embodiment is directed to a method of contactless scanning of any type of chargeable surface, such as chargeable surfaces used in applications such as xerography, ink jet printing, ionography, extrusion dies for coating, LED imaging, or LCM studies or testing. The following description of the illustrated embodiment concentrates on scanning of an imaging surface of a photoreceptor used in xerography and LCM studies for illustrative purposes, however the scope of the present disclosure is not limited to scanning thereof, but may be applied to scanning of other chargeable surfaces used in other applications.

Figure 1:
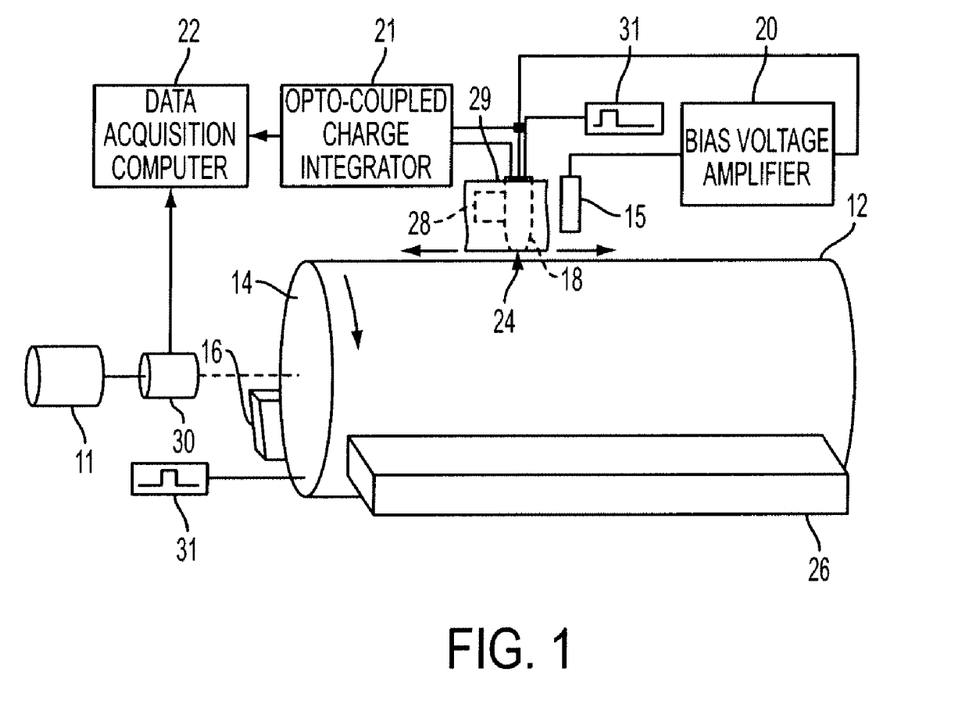
FIG. 1 is a schematic illustration of an embodiment of a scanner system in accordance with the present disclosure.

For a general understanding of the features of the illustrated embodiment, reference is made to the drawings, where like reference numerals have been used throughout to identify identical elements. With reference to FIG. 1, an exemplary scanner system 10 is shown including an electrically conductive and isolated drum 14 that is rotated at constant speed by a stepper motor 11. Similar to a xerographic imaging system, a chargeable surface embodied as a flexible photoreceptor 12 (which may be formed as a photoreceptor belt) is mounted on drum 14, and charged via a charging device 16, such as a scorotron which electrostatically charges the photoreceptor 12 to a constant voltage. The photoreceptor 12 is essentially a conductive bottom plate that functions as a ground plane to which the charge is applied. Alternatively, the drum 14 may be a photoreceptor drum substrate coated with at least one electrophotographic coating functioning as the photoreceptor 12. It is to be expressly understood that the current invention is not restricted to belts and that photoreceptors or other materials in a drum configuration or a flat plate x-y scanning system could also be studied with this system.

The system 10 further includes an electrostatic voltmeter probe 15 having its output coupled to a bias voltage amplifier 20, high resolution scanner probe 18 carried in a distance control system 29 and coupled to a charge integrator 21 which in turn has its output optically coupled to a signal amplifier (not shown) coupled to a data acquisition computer 22 to which the output of encoder 30 is coupled. Stepping actuator is mechanically coupled to probe 18 to control its movement with respect to photoreceptor 12. Optionally, at least one wave generator 31 has its output coupled to probe 18. The electrostatic probe 15 is coupled to the output of bias voltage amplifier 20 to bias the scanner probe 18 to within a predetermined threshold potential difference from the average surface potential of photoreceptor 12. In one embodiment of the disclosure, the electrostatic probe 15 is a low spatial resolution electrostatic voltmeter.

During scanning, the scanner probe 18, charge integrator 21 and data acquisition computer 22 measure changes in the potential of a selected spot or pixel on the photoreceptor 12 after charging. Measurements are obtained by applying a pulse from encoder 30 at a constant angular position. The encoder ensures a spatial registration of probe readings by the scanner probe 18 for forming an accurate map of the surface of the photoreceptor by supplying a once-per revolution pulse, such as a transistor-transistor logic (TTL) pulse which acts as a trigger for data acquisition of individual scan lines. The data acquisition includes an A/D conversion process which operates on a system clock, as described further below. The distance control system 29 controls the distance or gap between the scanner probe 18 and the surface being scanned (also referred to throughout the disclosure as the gap distance), e.g., the surface of the photoreceptor 12. This gap distance is maintained by the distance control system 29 through the process of aerodynamic floating and is well known to those skilled in the art. The at least one wave generator 31 applies a reference wave to either the ground plane of the photoreceptor 12 or the scanner probe 18 or both. The wave generator 31 is connected to the drum 14 using a suitable connector (such as a system of conductive brushes, not shown) for applying the reference wave to the photoreceptor 12. Alternatively, the wave generator 31 is connected to the shield 34.

Figure 3:
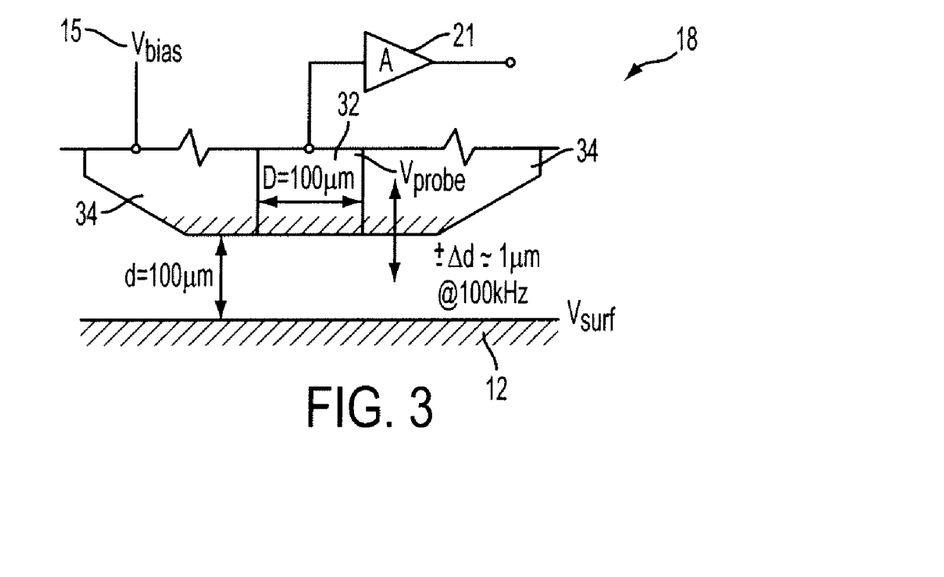
FIG. 3 is an illustration of the scanner probe employed in the scanner system shown in FIG. 1.

A lower end 24 of scanner probe 18 has a smooth surface which is parallel to and positioned above the outer imaging surface of photoreceptor 12 (typically about 100 μm above the outer imaging surface of photoreceptor 12 as depicted in FIG. 3). The time consumed by probe 18 to reach a section of photoreceptor 12, which has just been charged by charging device 16, allows a surface charge distribution to form before they are scanned by scanner probe 18. Charge on photoreceptor 12 may optionally be removed with a discharging device 26 shown in FIG. 1, such as an erase light, after photoreceptor 12 passes scanner probe 18.

The charge integrator 21 includes circuitry, such as an optoisolator circuit (not shown) having an optocoupled amplifier, for isolating the data acquisition computer 22 from the high voltage probe bias of the scanner probe 18. Optocoupled amplifiers are well known in the electronic art for providing an optical link between two electrical components which require perfect voltage isolation from each other, which is usually achieved by transmission of a signal without a continuous electrical connection by using an electrically driven light source and a light detector which is electrically insulated from the light source. Furthermore, as used herein, the term "circuit" shall be defined as any electrical element or combination of electrical elements, including electrical elements controlled by software, having a desired overall electrical function. The isolation of the scanner probe 18 from the data acquisition computer 22 allows biasing of the scanner probe 18 to the average surface potential of the photoreceptor 12 rather than biasing of the effective ground plane of the photoreceptor 12, thereby preventing air breakdown and arcing. The optically coupled charge integrator 21 provides the probe signal to data acquisition computer 22 where the probe signal is recorded and/or analyzed.

The scanner probe 18 senses changes in potential of the photoreceptor 12 and generates a corresponding analog probe signal. While the scanner probe 18 is described here as scanning the surface of the photoreceptor 12, this is only for illustrative purposes and it is to be expressly understood that the scanner probe 18 may scan any suitable surface that holds an electrostatic potential such as drum 14 itself. The charge integrator 21 signal conditions the probe signal to put the probe signal for processing by the data acquisition computer 22, which includes, for example, amplifying the probe signal.

Figure 6:
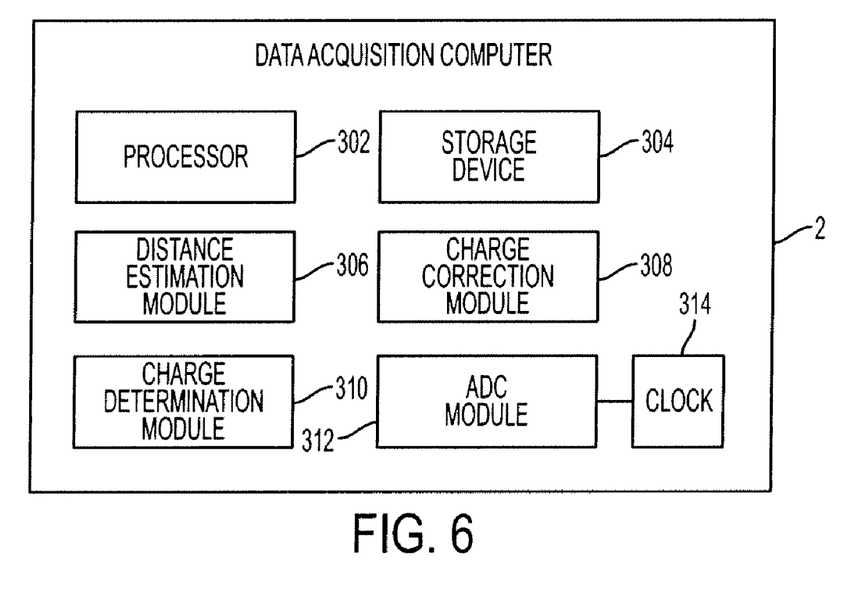
FIG. 6 is a block diagram of a data acquisition computer employed in the scanner system shown in FIG. 1.

As shown in FIG. 6, computer 22 includes a processor 302, system clock 314, and a clocked analog to digital conversion (ADC) module 312 for converting the probe signal to a digital signal. The converting process includes sampling the analog probe signal at a predetermined frequency (also referred to as the frequency of the ADC module 312) that is synchronized by clock 314, which corresponds to the operation of encoder 30. In the current example, the clock 314, which may be TTL compatible, generates about 20 000 pulses per revolution. The stepper motor 11 which rotates the drum 14 has a resolution of 20 000 steps per rotation. The clock 314 is also used to drive the stepper motor 11 at a given RPM (typically 60 RPM). Thus a 20 000 Hz TTL pulse train is used to drive the stepper motor 11 and derive the ADC module 312 from that using a frequency divider circuit to give a ADC module 312 frequency of half the main system clock 314, or about 10 000 Hz. This method permits the employment of synchronous delayed acquisition as a noise reduction measure. When the stepper motor 11 rotates, an undesirable noise spike is often detected in the data at that instance. By acquiring the ADC signals using a synchronous (but slightly delayed) clock 314, data is acquired at a point of the stepper cycle where the undesirable noise source is at a minimum. Finally, the once-per-revolution TTL pulse from the encoder 30 ensures that a line or scan of acquired data always begins at the same angular point on the drum 14. The encoder 30 once-per-revolution (or indexer) signal is decoupled from the clock 314 signal but is closely correlated. The digital probe signal, once converted, is in condition for processing by processor 302.

During a scan, the stepping actuator combination 28 (e.g., a stepper motor and micrometer screw combination) moves the scanner probe 18 to a new scan line position and the process is repeated for charging, measuring changes in charge and discharging the photoreceptor 12. The stepper actuator combination 28 allows the scanner probe 18 to scan the surface under test faster. In one embodiment, an array of spaced and/or staggered high resolution probes 18 are provided, where the array of high resolution probes 18 simultaneously scan along different respective scan lines.

Figure 2:
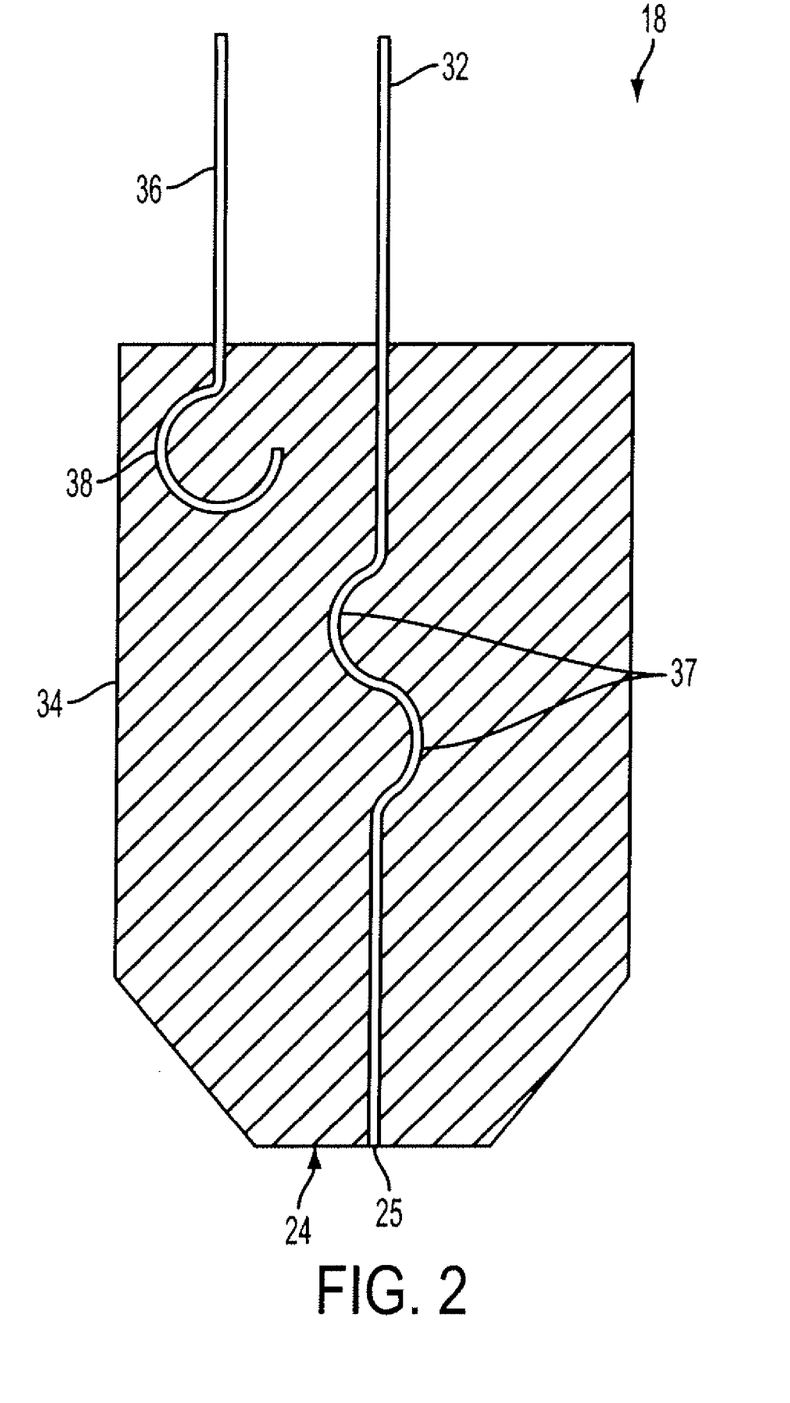
FIG. 2 is a schematic sectional side view in elevation of a scanner probe employed in the scanner system shown in FIG. 1.

With reference to FIGS. 2 and 3, an exemplary scanner probe 18 is shown. The scanner probe 18 includes a central electrode 32 having a lower end 25, and a shield electrode 34. The central electrode 32 and the shield electrode 34 are both formed of a conductive material, such as metal. The central electrode 32 is insulated from the shield electrode 34 by a thin insulative coating (not shown). The conductive material of center electrode 32 may be provided as a small diameter wire which is insulated by a very thin material. For example, the conductive material may be enameled, i.e., coated with a thin electrically insulating coating (not shown). Any suitable insulating coating may be utilized. Generally, the insulating coating is a film forming material having a resistivity in excess of about 1013 ohm/cm and a thickness between about 5 micrometers and about 50 micrometers. The cross-section of lower end 25 is generally circular, having a typical diameter of 113 µm. It is to be expressly understood however that other geometries other than what is described here could be used without departing from the original spirit and scope of the invention.

Center electrode 32 is embedded in shield electrode 34 which is electrically grounded via ground wire 36. Grounded shield electrode 34 is used as a shield against electromagnetic noise. Changes in potential are sensed by the embedded center electrode 32. Due to the arrangement of the center electrode 32 embedded within the shield electrode 34, the scanner probe 18 is well shielded from external noise and rendered suitably rugged.

A series of small bends 37 in the wire of center electrode 32 captured in electrode shield 34 prevents the tendency of the wire 32 to pull back into the shield or become recessed in the shield 34, and in some cases, pull out of the shield 34 entirely. The capacitive coupling between the end 25 of center electrode 32 and the outer imaging surface of photoreceptor 12 will change as the center electrode 32 retracts into the shield 34 thus adversely affecting readings. Ground wire 36 provides an electrical ground connection to the shield electrode 34. The ground wire 36 is provided with a loop 38 to maintain the ground wire's position 36 secured within the electrode shield 34.

The end 24 of scanner probe 18 is perpendicular to the centerline of high resolution probe 18, with the lower end 25 of the electrode 32 and the lower end of electrode shield 34 substantially flush with each other. If the center of electrode 32 is recessed too far into shield electrode 34, more electric flux will couple into the electrode shield 34 rather than onto the center electrode 32 thereby reducing the signal. If the lower end of center electrode 32 extends beyond electrode shield 34, it could scratch photoreceptor 12. Also by polishing, the lower end of center electrode 32 and the bottom of electrode shield 34 are at the same plane and thereby achieve good shielding and detection properties. Thus, excessive electric fields are prevented, the possibility of scratching the photoreceptor 12 is minimized, and shielding and detection properties of the scanner probe 18 are maximized.

It should be expressly understood that there are many ways to build a 100 um diameter flat polished probe. The above paragraphs describe only one such embodiment of doing so for illustrative purposes only and are not meant to be limiting in any way. A person skilled in the relevant art will readily understand that there are other equivalent ways to construct a probe that is robust to handling, well shielded electrostatically, and also well polished to conform with and to protect the surface under test.

A bias is applied to the electrode shield 34 by the amplified output of the electrostatic voltmeter probe 15. One may alternatively apply a bias on electrode shield 34 without using an electrostatic voltmeter probe 15, so long as the applied bias is within a predetermined voltage range (±300 V in the current example) of the average surface potential on the outer imaging surface of the photoreceptor 12. The output monitor signal of the low resolution electrostatic probe 15 can be used to drive a high-voltage amplifier (not shown) whose output is in turn connected to the scanner probe 18 in such a way that the high voltage amplifier follows the surface voltage sensed by probe 15.

The combination of the lower end 25 of the center electrode 32 and the outer imaging surface of photoreceptor 12 forms a small parallel plate capacitor. It is through the capacitance formed by this parallel plate capacitor that a latent image is detected. For illustration purposes, at a typical gap distance of 100 µm between probe end 24 (e.g., the end 25 of center electrode 32) and the outer imaging surface of photoreceptor 12, the capacitance is found to be approximately 1 fF, using the approximate relation:

$$C_{coupling} = A\epsilon_0/d \qquad (1)$$

where $C_{coupling}$ is the capacitance induced; A is the area of the surface at the lower end 25 of the center electrode 32 (acting as one end of a parallel plate capacitor); $\epsilon_o$ is the permittivity of free space (a physical constant); and d is the gap distance between the capacitor plates formed by the photoreceptor 12 and the scanner probe 18. In one embodiment, the gap distance is between about 20 micrometers and about 200 micrometers, and in another embodiment between about 50 micrometers and about 100 micrometers. When the gap distance is less than about 20 micrometers, there is increased risk of probe 18 touching the surface of photoreceptor 12 which can lead to erroneous results. When the gap distance is greater than about 200 micrometers, the probe sensitivity and resolution may be substantially reduced.

When a charge of 0.1 pC is present, in accordance with (Q=CV) the voltage across the capacitance 1 fF is 100 V on the probe end 24. The surface potential can be determined by using the capacitance-voltage relationship Q=CV, as $$V_{surface} = Qd/A\epsilon_0; \qquad (2)$$

where $V_{surface}$ is the surface potential; and Q is the surface charge.

Equation 1 above gives:

$$C_{coupling} = A\epsilon_0/d \qquad (3)$$

Inverting this equation gives a calibration curve:

$$1/C_{coupling} = (1/A\epsilon_0)d \qquad (4)$$

Since V is directly proportional to the gap distance, d, it is important to keep the gap distance d constant during scanning to obtain meaningful results. This is complicated by the fact that the drum 14 on which the photoreceptor 12 is mounted may be slightly eccentric, such eccentricities typically ranging between ±25 µm. Other mechanical factors that may cause variations in d, include play in bearings associated with the drum 14, play and strain or tension in a air hose tube, of the aerodynamic floating device for supplying gas, misalignment of the scanner probe 18, and variations on the surface 45 of the photoreceptor 12. Also, play may be present in any electrical cables that connect to the probe system. Precise machining of the scanner mechanical hardware, such as the mounting drum 14 and related drum bearings, and reducing vibrations from the stepper motor 11 by selecting a smooth running microstepping motor helps to reduce excessive measurement errors due to variations in d.

Distance control system 29 further reduces variations in the gap distance. The distance control system 29 may be an active distance control system having active control equipment, or a passive distance control system. An example of a passive distance control system including an aerodynamically floating device is described in U.S. Pat. No. 6,119,536, which is hereby incorporated by reference in its entirety. However, slight variations in the gap distance may still exist, and a need exists to determine the slight variations in the gap distance and to correct the potential readings for the determined variations. Such variations may be due to changes over time in the tension of a cable for scanner probe 18 and/or an air hose of the aerodynamic floating device, misalignment of the scanner probe 18, eccentricity of the drum 14, shifts in bearings associated with the drum 14, etc. Reproducibility of an initial gap distance is difficult. Accordingly, it is difficult to achieve a desired initial gap distance when replacing the scanner probe 18. Corrections for variations in the gap distance and slight induced charge variations are then carried out.

As shown in FIG. 3 and as mentioned above, the scanner probe 18, the surface of the photoreceptor 12, and the small air gap between the two forms an approximation of a parallel plate capacitor where the surface of the photoreceptor 12 is at an electrostatic potential $V_0$. The scanning probe 18 has a natural resonance frequency at around 200 Hz. This resonance can be excited by aiming a continuous jet of compressed air at the base of the air gap between the scanner probe 18 and the photoreceptor 12. However other ways of inducing a driven oscillation in the probe subsystem may be used including but not limited to pneumatic excitation with pressurized gas, mechanical means such as a wound-up spring, and electro-mechanical or electro-acoustic means such as mechanisms similar to a loudspeaker voice coil or a solenoid. Additionally, piezoelectric elements would be highly desirable since piezoelectric elements can be easily obtained that are generally fairly compact, lightweight, and can be driven electrically at high frequency. Higher frequencies will increase the detectable signal and signal-to-noise of the system and, if driven above 20 kHz, will ensure that any acoustic emissions are inaudible to human operators of the instrument.

Additionally, the current invention has the ability to perform 'standard' distance corrections for non-point-like distance effects, if required. This would use employ reference signals from the generator 31. As discussed above, this method is less sensitive to small changes in distance and that in combination with aerodynamic floating, is sufficient to maintain a constant average air gap distance.

Figure 4:
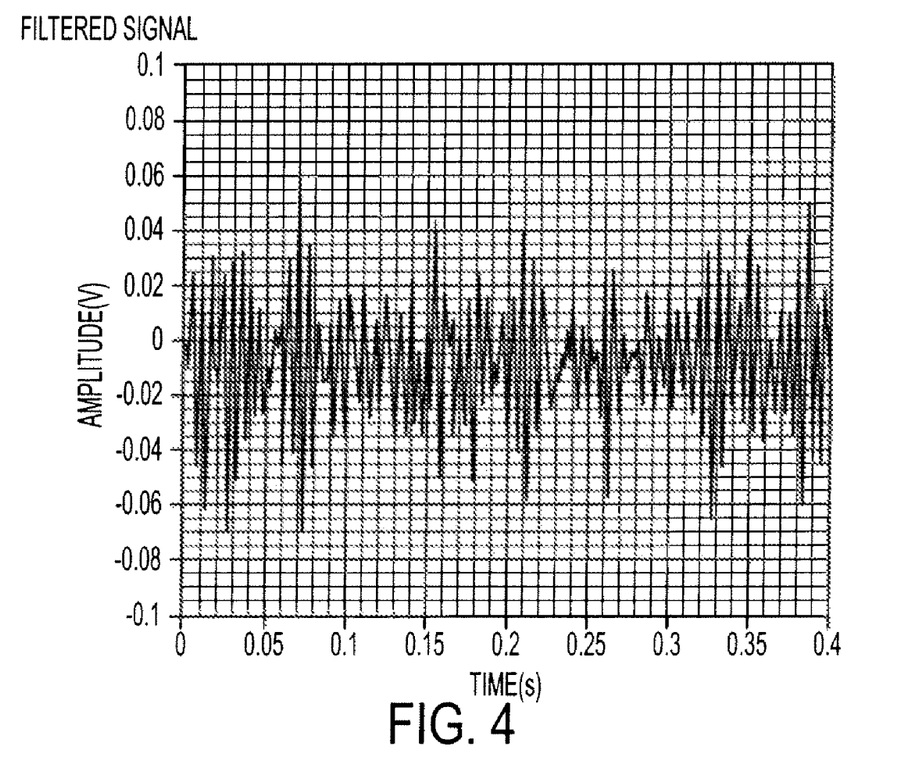
FIG. 4 is a plot of experimentally determined amplitude of the probe AC signal plotted for a time interval when the probe is vibrating and there is a voltage difference between it and the drum shown in FIG. 1.

With the scanner probe 18 vibrating with an amplitude of 1 μm at about 100 kHz, a peak AC current of about 4 pA is induced. This peak current is measurable whenever the probe is vibrating and there is a voltage differential between the scanner probe 18 and the surface of the photoreceptor 12. FIG. 4 shows the results of when an oscilloscope (not shown) is coupled to the output of the probe amplifier (also not shown). The signal shown is for an example potential difference of 100 VDC between the probe and surface and can optionally be digitally filtered at 250 Hz to remove high-frequency noise from the environment 28 and 11.

With the scanner probe 18 vibrating, the induced current is sensed and a feedback system using analog or digital means generally well understood by those skilled in the art. The output of the feedback system connected to a high voltage amplifier 20, whose output biases the probe 18 as seen in FIG. 3. The feedback system increases the bias voltage of the scanner probe 18 in such a way as to match the $V_0$ of the surface of the photoreceptor 12 and null the vibration-induced current, that is to say to force $\Delta V$ to equal zero. Each absolute voltage for each scanned area of photoreceptor 12 is recorded and then can be plotted as a digital image. If the probe is biased to a DC voltage, $V_{probe}$, and the surface under the probe is at a locally constant potential, $V_{surface}$, then there will be a DC voltage difference ($V_{surface}-V_{probe}$). The probe's charge amplifier is not sensitive to DC signals, so for a static system with a DC voltage difference no signal will be detected. However, by inducing a forced up and/or down vibration in the probe a small current signal is induced, which is detectable by the charge amplifier. The presence of a signal during vibration therefore indicates that there is a non-zero voltage difference between the probe and the surface. The probe bias is then adjusted in such a way as to null or minimize the induced signal. When this signal reaches a minimum (failure to reach zero or null is due to noise and other uncontrollable outside factors) it is then known that the potential difference between the probe and surface must be zero. To control and measure the probe bias voltage, so we know that the surface (locally) must be at the same potential. This was demonstrated in the Invention Disclosure. Only when $\Delta V$ is zero will the current also be zero. Typically approximately 4000 electrons are resolved using this technique. This result corresponds to a 1V resolution for the probe geometries that are described here.

Figure 5:
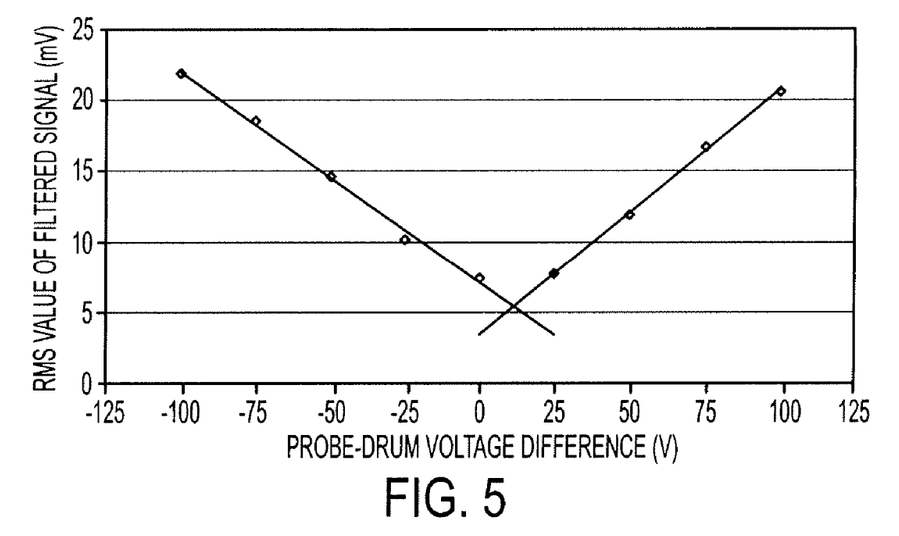
FIG. 5 is a plot of experimentally determined RMS values of the filtered probe signal plotted for various probe-drum voltage differences.

In FIG. 5, the probe-drum potential difference is plotted against the root mean squares (RMS) value of the filtered signal. The plot clearly shows that the RMS value of the signal reaches a minimum value near zero, which indicates that the scanner probe 18 has reached the same potential as the surface under investigation, namely the surface of the photoreceptor 12 in this illustration. The zero-discrepancy is due to a DC offset in the voltage amplifier 20. This offset can be easily compensated out using techniques well known in the art.

Many alterations and modifications may be made by those having ordinary skill in the art without departing from the spirit and scope of the present embodiments. Therefore, it must be understood that the illustrated embodiment has been set forth only for the purposes of example and that it should not be taken as limiting the invention as defined by the following invention and its various embodiments. For example, many other techniques such as applying a mechanical or electromagnetic force and can be used in addition to aiming a jet of compressed air when making the scanner probe 18 vibrate at a selected frequency. Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

Various exemplary embodiments encompassed herein include a method of imaging which includes generating an electrostatic latent image on a xerographic surface by uniformly charging a photoreceptor; a thermoplastic toner is then transferred to the charged area by electrostatic attraction and the developed image is fixed in a fusing process involving the application of heat and pressure.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

We claim:

1. A contactless system for sensing electrostatic potential on a chargeable surface comprising:
   a first circuit for charging the chargeable surface to receive and hold a first voltage charge;
   a scanner probe having a probe surface, the probe surface being displaced a distance from the chargeable surface;
   second circuit for biasing the scanner probe to a scanner probe bias voltage within a predetermined voltage threshold of the first voltage charge;
   a capacitor formed of the chargeable surface, a dielectric material between the scanner probe surface and the chargeable surface, and the scanner probe surface, wherein the scanner probe senses a potential associated with an applied charge on the chargeable surface;
   a device for inducing an oscillating current in the scanner probe that results in the scanner probe vibrating;
   a third circuit for sensing the vibration-induced oscillating current in the scanner probe;
   a processor; and
   a charge determination module including programmable instructions executable by the processor for determining a potential of a specific location on the chargeable surface based on the scanner probe reading and the vibration-induced oscillating current in the scanner probe, including charge migration on the chargeable surface,
   and adjusting the scanner probe bias voltage to null the vibration-induced oscillating current in the scanner probe.

2. The contactless system of claim 1, wherein the charge determination module determines the potential of a specific location based on sensing the absolute surface potential.

3. The contactless system of claim 1, further comprising:
   a mechanism establishing relative movement between the scanner probe and the chargeable surface and for scanning the chargeable surface for electrostatic potentials as the chargeable surface and the scanner probe move relative to one another; and
   a device maintaining the average distance between the scanner probe surface and the chargeable surface constant as the relative movement is established between the scanner probe and the chargeable surface.

4. The contactless system of claim 3, further comprising an average distance correction module including programmable instructions executable by the processor for determining the distance between the scanner probe surface and the chargeable surface at a location where the chargeable surface is being scanned based on the scanner probe readings and a previously generated calibration curve.

5. The contactless system of claim 1, wherein the chargeable surface is a photoreceptor imaging surface of a xerographic system.

6. The contactless system of claim 1, wherein the device for inducing an oscillating current in the scanner probe is a piezoelectric motor coupled to the scanner probe, wherein the piezoelectric motor causes the scanner probe to oscillate at a selected frequency.

7. The contactless system of claim 1, where the third circuit for sensing the vibration-induced current in the scanner probe further comprises a mechanism for filtering the vibration-induced current to remove high-frequency noise produced by the contactless system, the local environment, or other sources.

8. A method for sensing electrostatic potentials on a chargeable surface comprising:
   charging the chargeable surface to receive and hold a first voltage charge;
   spacing a surface of a scanner probe a distance from the chargeable surface;
   biasing the scanner probe to a second voltage charge within a predetermined voltage threshold of the first voltage charge, wherein a capacitor is formed from a combination of the chargeable surface, a dielectric substance between the scanner probe and the chargeable surface, and the scanner probe;
   oscillating the scanner probe at a selected frequency of the scanner probe in order to induce a current in the scanner probe and cause the scanner probe to vibrate;
   sensing the vibration induced current in the scanner probe;
   applying a reference voltage to at least one of the scanner probe and the chargeable surface; and
   determining a potential of a specific location on the chargeable surface based on scanner probe reading by adjusting the reference voltage to null the vibration-induced current in the scanner probe.

9. The method of claim 8, wherein determining the potential of a specific location comprises sensing the absolute surface potential at that location.

10. The method of claim 8, further comprising:
    establishing relative movement between the scanner probe and the chargeable surface to scan the chargeable surface for electrostatic potentials as the chargeable surface and the scanner probe move relative to one another; and
    maintaining a constant average distance between the scanner probe surface and the chargeable surface as the relative movement is established between the scanner probe and the chargeable surface.

11. The method of claim 10, further comprising determining the average distance between the scanner probe surface and the chargeable surface at the location where the chargeable surface is being scanned based on the scanner probe reading and a previously generated calibration curve.

12. The method of claim 8, wherein charging the chargeable surface comprises charging a photoreceptor imaging surface of a xerographic system.

13. The method of claim 8, wherein oscillating the scanner probe at a selected frequency comprises is performed by a piezoelectric vibrating element coupled to the scanner probe.

14. The method of claim 8, where sensing the vibration-induced current in the scanner probe further comprises filtering the vibration-induced signal to remove any extraneous high-frequency noise.

15. A contactless scanning system for sensing electrostatic potential on a photoreceptor comprising:
- a first circuit for charging the photoreceptor to receive and hold a first voltage charge;
- a scanner probe having a probe surface, the probe surface being displaced a distance from the photoreceptor;
- a second circuit for biasing the scanner probe to a scanner probe bias voltage within a predetermined voltage threshold of the first voltage charge, wherein a capacitor is formed by a combination of the photoreceptor, a dielectric material between the scanner probe surface and the photoreceptor, and the scanner probe;
- wherein the scanner probe senses a potential associated with an applied charge on the photoreceptor;
- a device for mechanically inducing an oscillating-current in the scanner probe which causes the scanner probe to vibrate;
- a third circuit for sensing the vibration-induced oscillating current in the scanner probe;
- a processor;
- a charge determination module including programmable instructions executable by the processor for determining a potential of a specific location on the photoreceptor based on the scanner probe reading of the vibration-induced oscillating current in the scanner probe; and
- a fourth circuit for adjusting the scanner probe bias voltage to null the vibration-induced current in the scanner probe.

16. The scanning system of claim 15, further comprising:
- a mechanism establishing relative movement between the scanner probe and the photoreceptor for scanning the photoreceptor for electrostatic potentials as the photoreceptor and the scanner probe move relative to one another; and
- a device maintaining the average distance between the scanner probe surface and the photoreceptor constant as the relative movement is established between the scanner probe and the photoreceptor.

17. The scanning system of claim 16, further comprising an average distance correction module including programmable instructions executable by the processor for determining the distance between the scanner probe surface and the photoreceptor at the location where the photoreceptor is being scanned based on the scanner probe reading and a previously generated calibration curve.

18. The scanning system of claim 15, where the device for inducing an oscillating current in the scanner probe is a compressed air jet directed at the scanner probe, wherein the compressed air jet causes the scanner probe to vibrate at a selected frequency.

19. The scanning system of claim 15, where the third circuit for sensing the induced current in the scanner probe further comprises a mechanism for digitally filtering the induced current to remove high-frequency noise produced by the scanning system.

20. The scanning system of claim 15, wherein the charge determination module comprises a mechanism sensing the absolute surface potential.

* * * * *